(12) United States Patent
Castellvi et al.

(10) Patent No.: US 9,414,861 B2
(45) Date of Patent: Aug. 16, 2016

(54) DYNAMIC STABILIZATION DEVICE

(75) Inventors: Antonio E. Castellvi, Tampa, FL (US);
Scott A. Webb, Clearwater, FL (US);
Craig Corrance, Lake Mary, FL (US);
John Kapitan, Waxhaw, NC (US); Gert Nijenbanning, LZ Hengelo (NL)

(73) Assignee: TRANSCENDENTAL SPINE, LLC, Mars, PA (US)

( * ) Notice: Subject to any disclaimer, the term of this patent is extended or adjusted under 35 U.S.C. 154(b) by 1392 days.

(21) Appl. No.: 12/028,506

(22) Filed: Feb. 8, 2008

(65) Prior Publication Data

US 2008/0195208 A1    Aug. 14, 2008

Related U.S. Application Data

(60) Provisional application No. 60/889,169, filed on Feb. 9, 2007.

(51) Int. Cl.
*A61B 17/70* (2006.01)

(52) U.S. Cl.
CPC ......... *A61B 17/7023* (2013.01); *A61B 17/7004* (2013.01); *A61B 17/7025* (2013.01); *A61B 17/7041* (2013.01)

(58) Field of Classification Search
CPC .......... A61B 17/7019; A61B 17/7023; A61B 17/7025; A61B 17/7031; A61B 17/7026; A61B 17/7028; A61B 17/7029; A61B 17/7002; A61B 17/7004; A61B 17/7005; A61B 17/7007; A61B 17/7008; A61B 17/701; A61B 17/7011

USPC .......................................... 606/254–262, 264
See application file for complete search history.

(56) References Cited

U.S. PATENT DOCUMENTS

| | | |
|---|---|---|
| 4,743,260 A | 5/1988 | Burton |
| 5,180,393 A | 1/1993 | Commarmond |
| 5,282,863 A | 2/1994 | Burton |
| 5,375,823 A | 12/1994 | Navas |
| 5,415,661 A | 5/1995 | Holmes |
| 5,423,816 A | 6/1995 | Lin |
| 5,480,401 A | 1/1996 | Navas |
| 5,529,420 A | 6/1996 | Henkel et al. |
| 5,536,268 A | 7/1996 | Griss |
| 5,672,175 A | 9/1997 | Martin |
| 5,752,955 A | 5/1998 | Errico |
| 5,803,924 A | 9/1998 | Oni et al. |

(Continued)

FOREIGN PATENT DOCUMENTS

| | | |
|---|---|---|
| WO | 0145576 | 6/2001 |
| WO | 02102259 | 12/2002 |

*Primary Examiner* — Jan Christopher Merene
*Assistant Examiner* — Atiya Mahmud
(74) *Attorney, Agent, or Firm* — Clements Bernard PLLC; Christopher L. Bernard; Lawrence A. Baratta, Jr.

(57) ABSTRACT

A surgical implant device for controlling the movement between a first bone or tissue portion and a second bone or tissue portion includes a first elongated member connectable for movement with the first bone or tissue portion and a second elongated member connectable for movement with the first bone or tissue portion. The first elongated member and the second elongated member are connected by a flexible joint configured to allow the first elongated member to pivot, move axially, and/or rotate relative to the second elongated member. At least one resilient member is associated with the flexible joint to resist relative movement of the first elongated member relative to the second elongated member.

16 Claims, 13 Drawing Sheets

(56) References Cited

U.S. PATENT DOCUMENTS

| | | | |
|---|---|---|---|
| RE36,221 E | 6/1999 | Breard et al. | |
| 5,961,516 A | 10/1999 | Graf | |
| 6,053,917 A | 4/2000 | Sherman et al. | |
| 6,162,223 A | 12/2000 | Orsak et al. | |
| 6,241,730 B1 | 6/2001 | Alby | |
| 6,267,764 B1 | 7/2001 | Elberg | |
| 6,296,644 B1 | 10/2001 | Saurat et al. | |
| 6,328,741 B1 | 12/2001 | Richelsoph | |
| 6,626,904 B1 | 9/2003 | Jammet et al. | |
| 6,875,211 B2 | 4/2005 | Nichols et al. | |
| 6,887,241 B1 | 5/2005 | McBride et al. | |
| 6,887,242 B2 | 5/2005 | Doubler | |
| 6,923,811 B1 | 8/2005 | Carl et al. | |
| 6,966,910 B2 | 11/2005 | Ritland | |
| 6,986,771 B2 | 1/2006 | Paul et al. | |
| 6,989,011 B2 | 1/2006 | Paul et al. | |
| 6,991,632 B2 | 1/2006 | Ritland | |
| 7,018,376 B2 | 3/2006 | Webb et al. | |
| 7,018,379 B2 | 3/2006 | Drewry et al. | |
| 7,029,475 B2 | 4/2006 | Panjabi | |
| 7,041,136 B2 | 5/2006 | Goble et al. | |
| 7,083,621 B2 | 8/2006 | Shaolian et al. | |
| 7,083,622 B2 | 8/2006 | Simonson | |
| 7,125,410 B2 | 10/2006 | Freudiger | |
| 7,207,992 B2 | 4/2007 | Ritland | |
| 2002/0133155 A1 | 9/2002 | Ferree | |
| 2003/0171749 A1 | 9/2003 | Le Couedic et al. | |
| 2003/0220643 A1 | 11/2003 | Ferree | |
| 2004/0002708 A1 | 1/2004 | Ritland | |
| 2004/0049189 A1 | 3/2004 | Le Couedic et al. | |
| 2004/0049190 A1 | 3/2004 | Biedermann et al. | |
| 2004/0073215 A1 | 4/2004 | Carli | |
| 2004/0225289 A1 | 11/2004 | Biedermann et al. | |
| 2004/0267260 A1 | 12/2004 | Mack et al. | |
| 2005/0065515 A1 | 3/2005 | Jahng | |
| 2005/0085815 A1 | 4/2005 | Harms et al. | |
| 2005/0090821 A1 | 4/2005 | Berrevoets et al. | |
| 2005/0113927 A1* | 5/2005 | Malek | 623/17.16 |
| 2005/0124991 A1 | 6/2005 | Jahng | |
| 2005/0154390 A1 | 7/2005 | Biedermann et al. | |
| 2005/0165396 A1 | 7/2005 | Fortin et al. | |
| 2005/0171543 A1 | 8/2005 | Timm et al. | |
| 2005/0177156 A1 | 8/2005 | Timm et al. | |
| 2005/0182400 A1 | 8/2005 | White | |
| 2005/0182401 A1 | 8/2005 | Timm et al. | |
| 2005/0203519 A1 | 9/2005 | Harms et al. | |
| 2005/0261682 A1 | 11/2005 | Ferree | |
| 2005/0261685 A1* | 11/2005 | Fortin et al. | 606/61 |
| 2005/0288670 A1 | 12/2005 | Panjabi et al. | |
| 2006/0009768 A1 | 1/2006 | Ritland | |
| 2006/0036240 A1 | 2/2006 | Colleran et al. | |
| 2006/0041259 A1 | 2/2006 | Paul et al. | |
| 2006/0058792 A1 | 3/2006 | Hynes | |
| 2006/0064090 A1 | 3/2006 | Park | |
| 2006/0084982 A1 | 4/2006 | Kim | |
| 2006/0084987 A1* | 4/2006 | Kim | 606/61 |
| 2006/0129147 A1 | 6/2006 | Biedermann et al. | |
| 2006/0142758 A1 | 6/2006 | Petit | |
| 2006/0149229 A1 | 7/2006 | Kwak et al. | |
| 2006/0149383 A1 | 7/2006 | Arnin et al. | |
| 2006/0189985 A1 | 8/2006 | Lewis | |
| 2006/0212033 A1 | 9/2006 | Rothman et al. | |
| 2006/0229613 A1 | 10/2006 | Timm et al. | |
| 2006/0247637 A1 | 11/2006 | Colleran et al. | |
| 2006/0264935 A1 | 11/2006 | White | |
| 2006/0264937 A1 | 11/2006 | White | |
| 2006/0264940 A1 | 11/2006 | Hartmann | |
| 2006/0271051 A1 | 11/2006 | Berrevoets et al. | |
| 2006/0282080 A1 | 12/2006 | Albert et al. | |
| 2007/0005137 A1 | 1/2007 | Kwak | |
| 2007/0016193 A1 | 1/2007 | Ritland | |
| 2007/0043356 A1 | 2/2007 | Timm et al. | |
| 2007/0049936 A1 | 3/2007 | Colleran et al. | |
| 2007/0100341 A1 | 5/2007 | Reglos et al. | |
| 2007/0123865 A1 | 5/2007 | Schlapfer et al. | |
| 2007/0123866 A1 | 5/2007 | Gerbec et al. | |
| 2007/0135815 A1 | 6/2007 | Gerbec et al. | |
| 2007/0196166 A1* | 8/2007 | Rogeau et al. | 403/120 |
| 2008/0183212 A1* | 7/2008 | Veldman et al. | 606/254 |

* cited by examiner

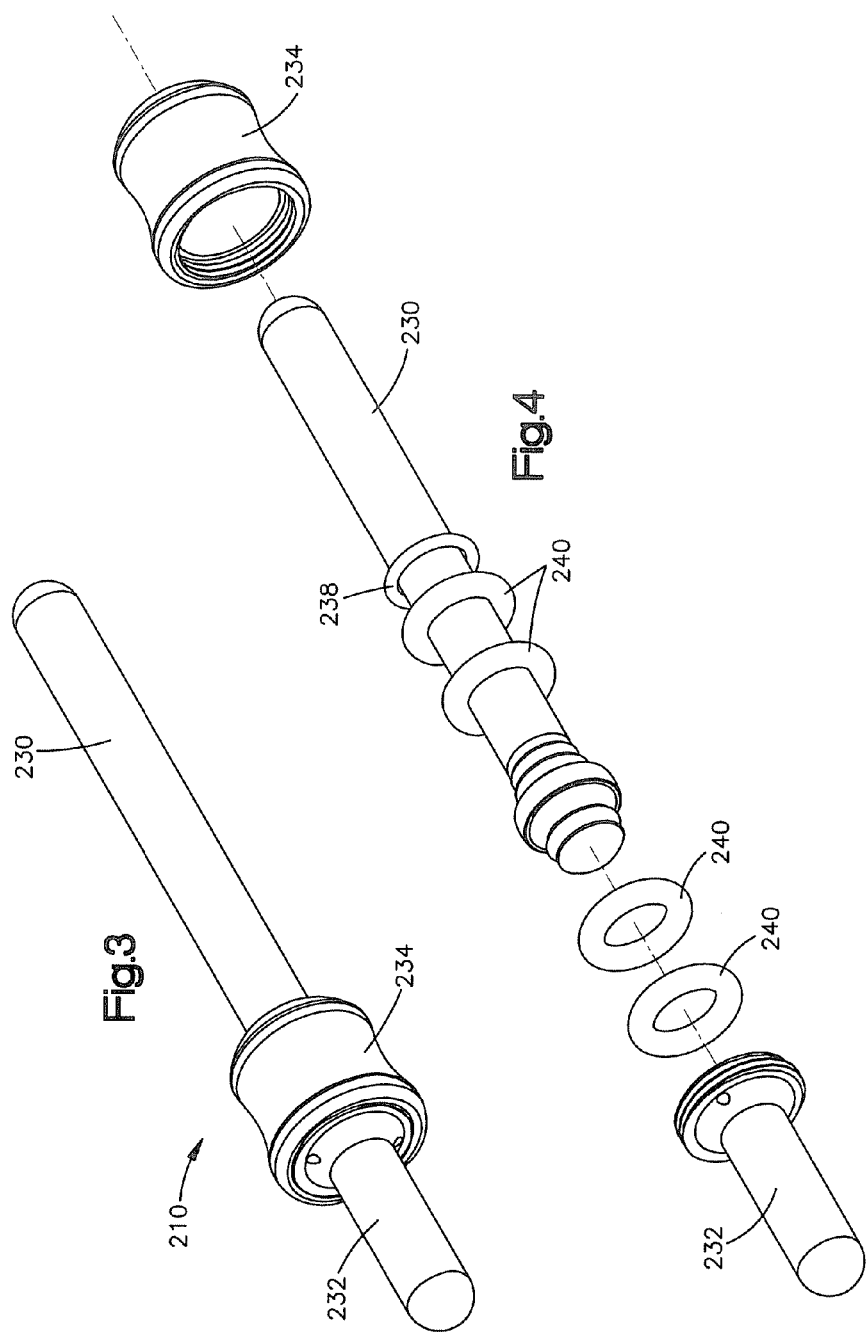

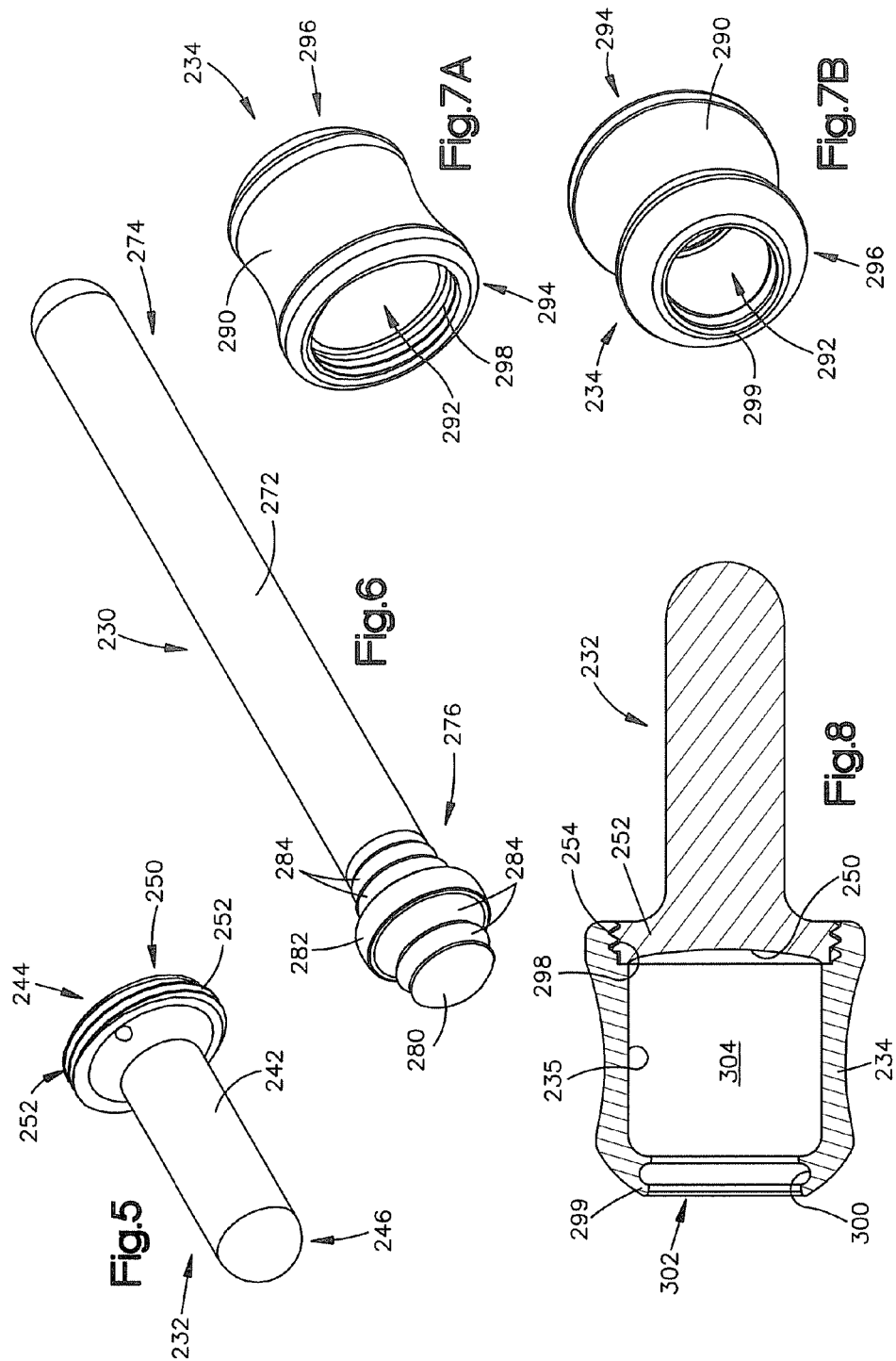

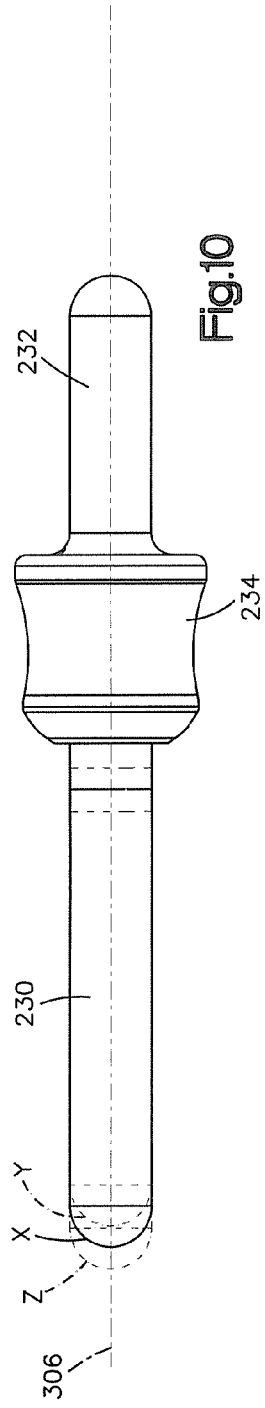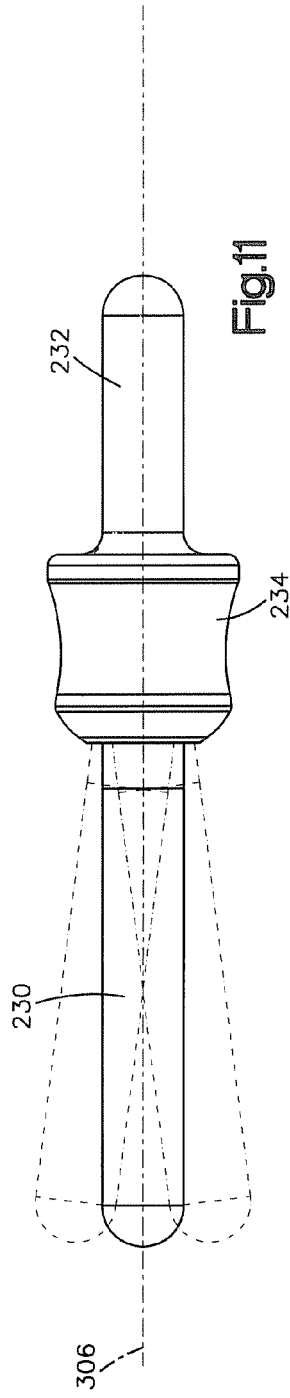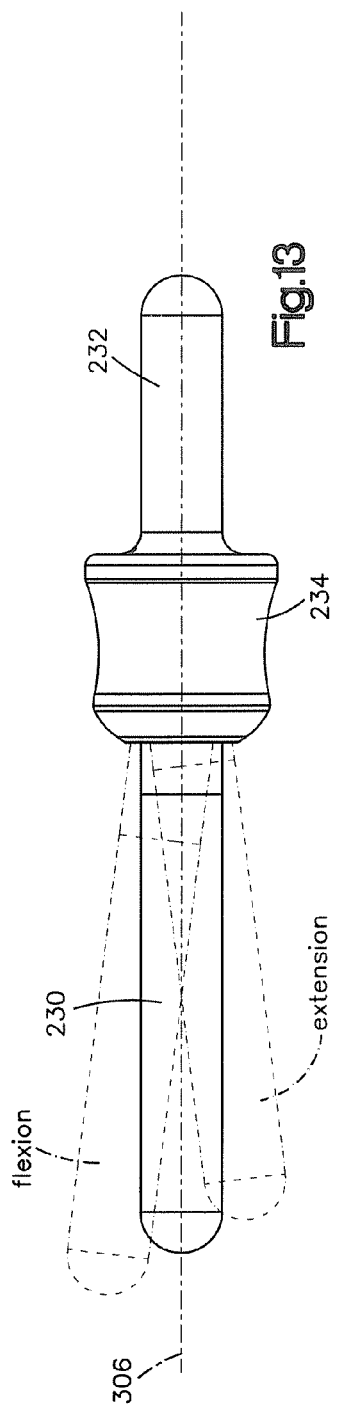

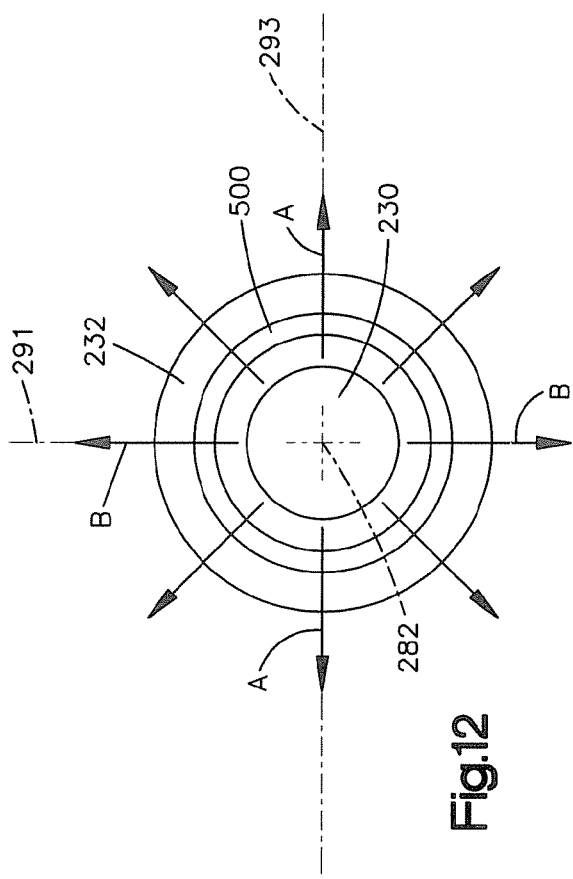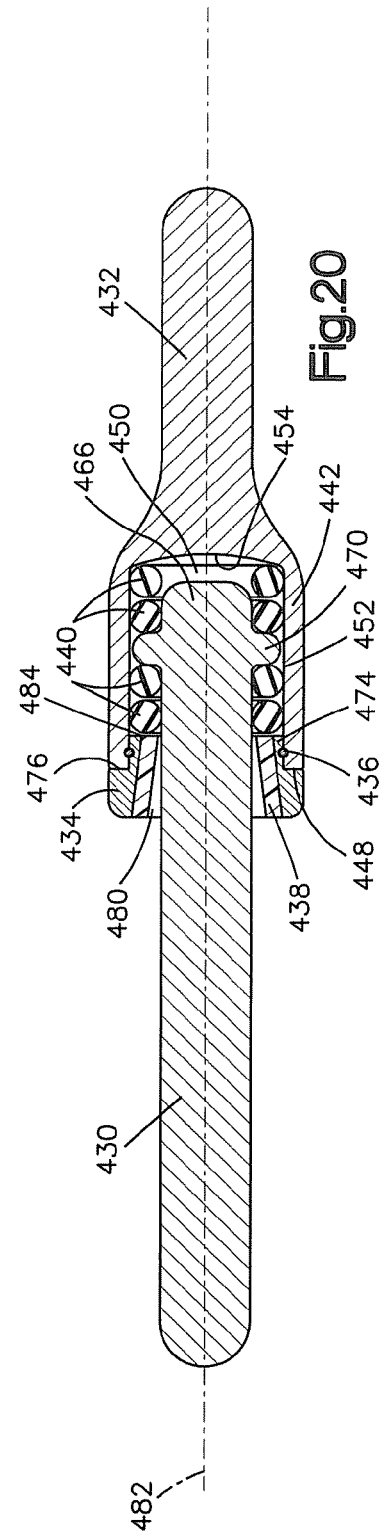

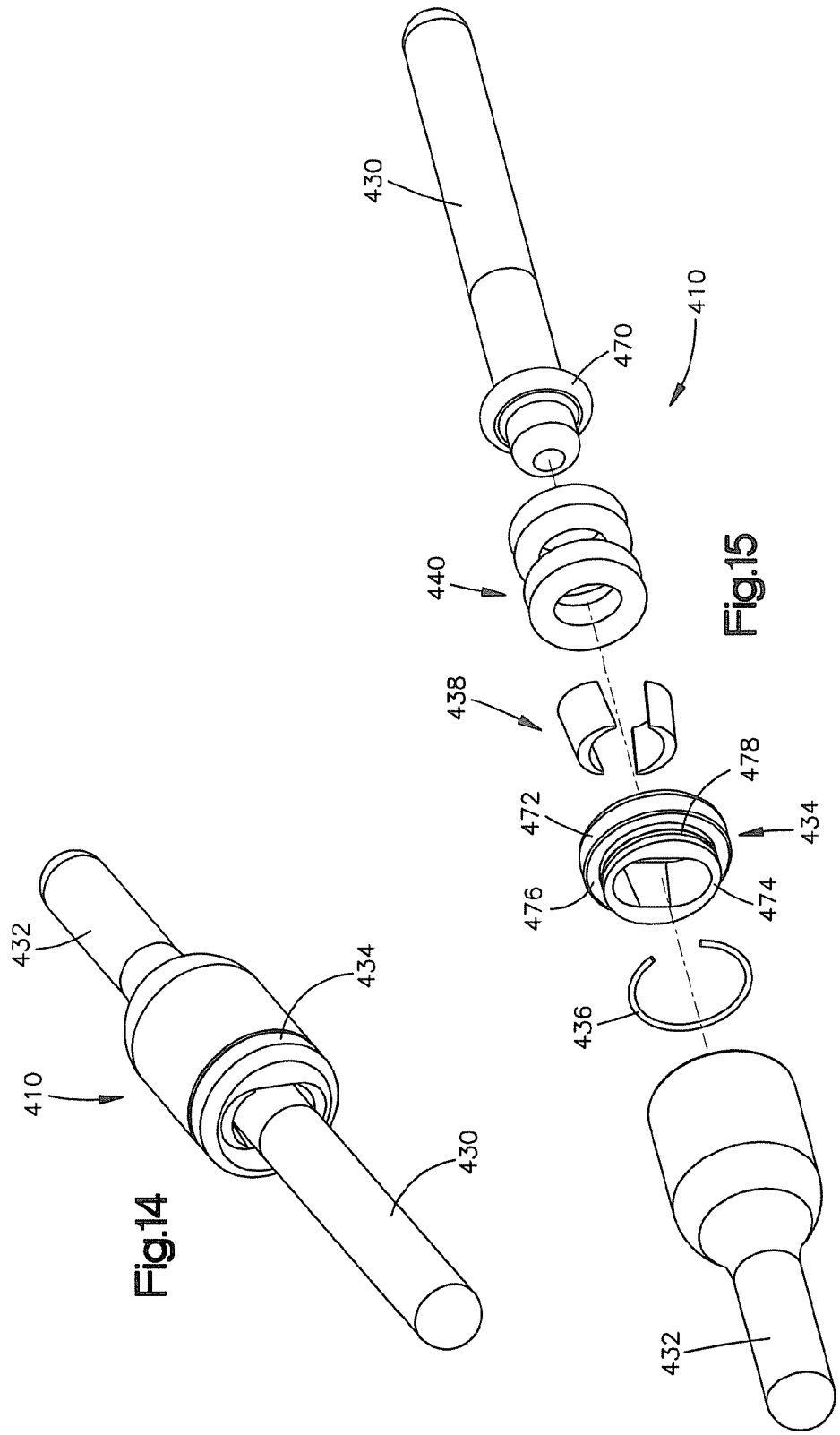

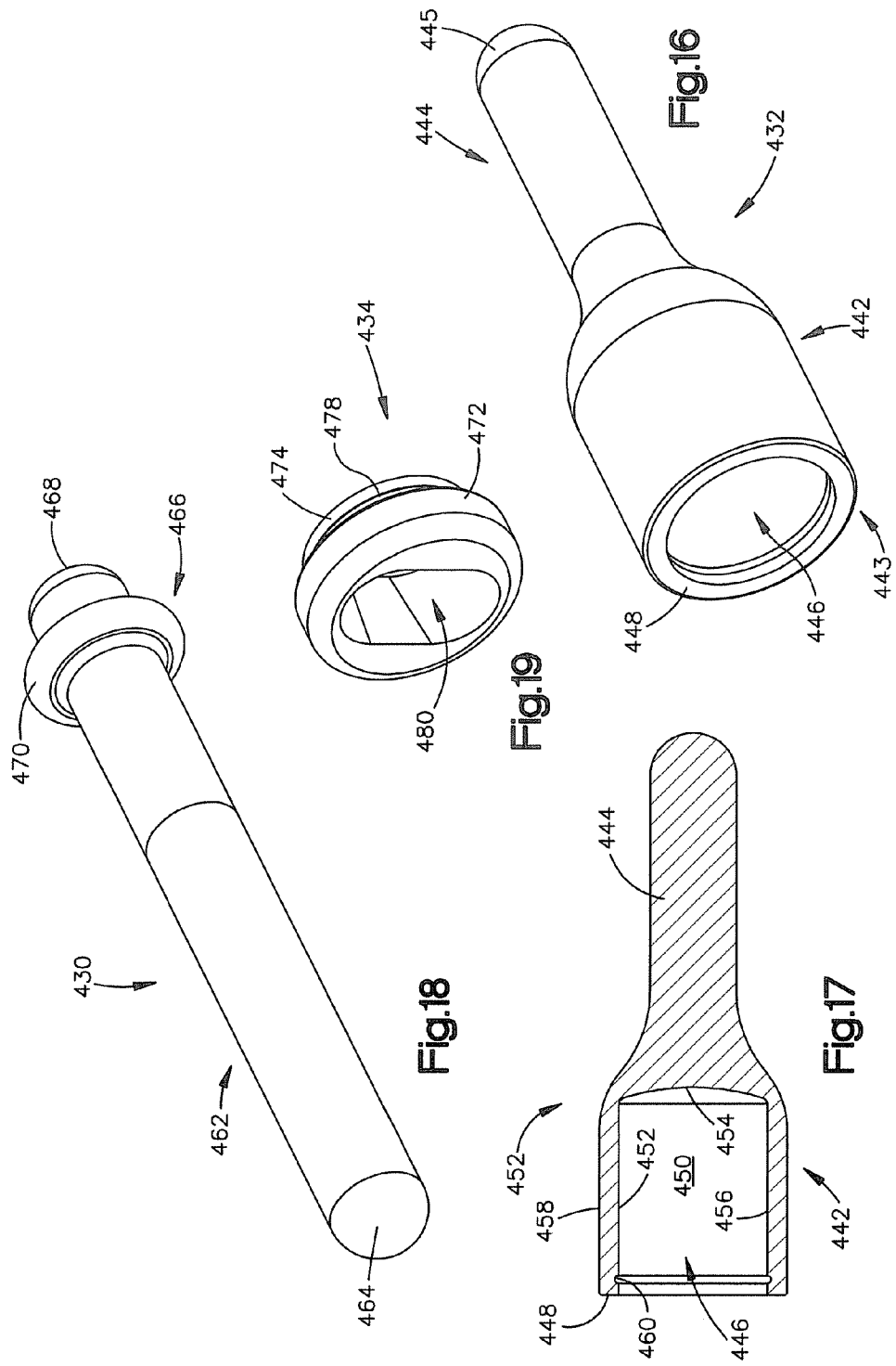

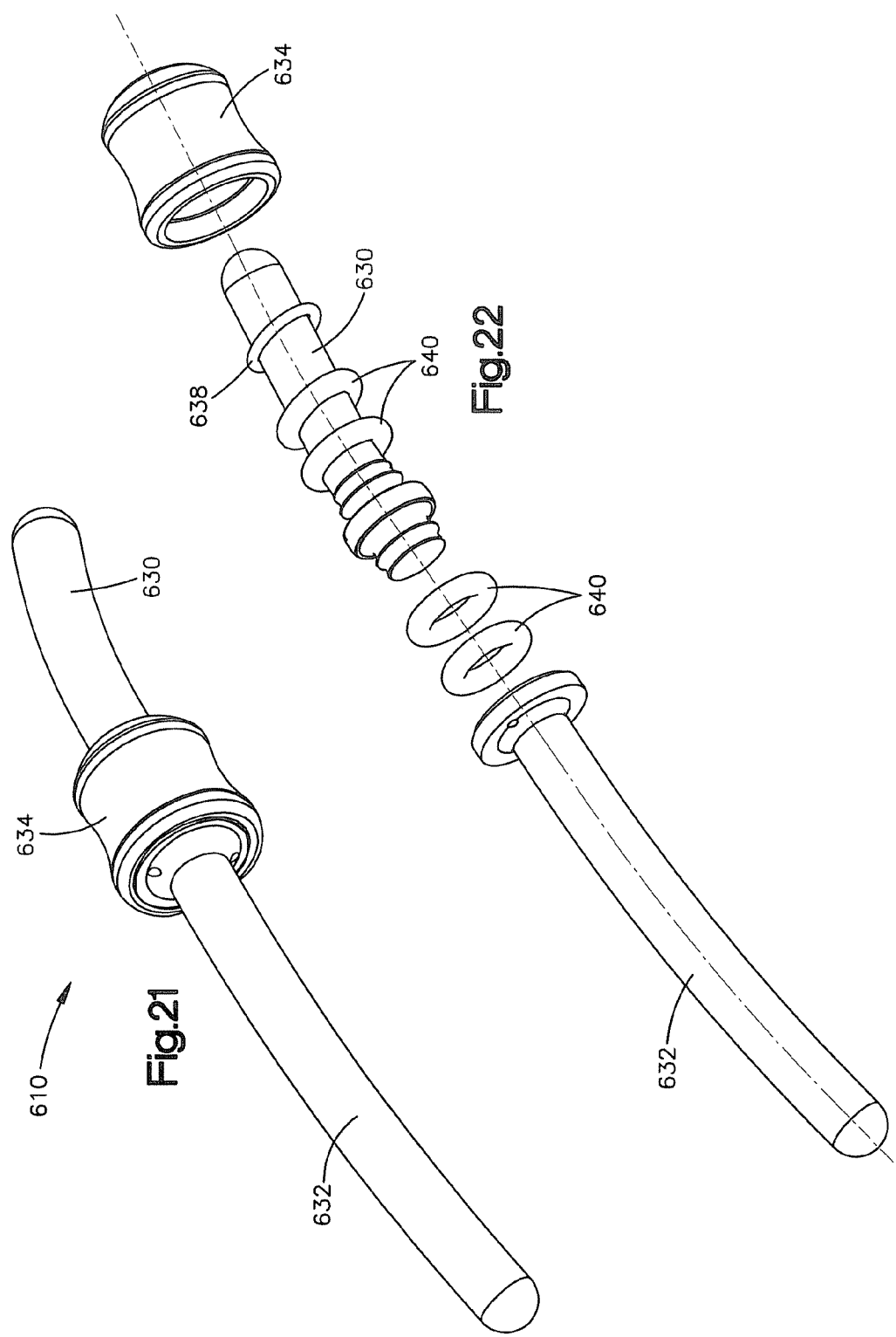

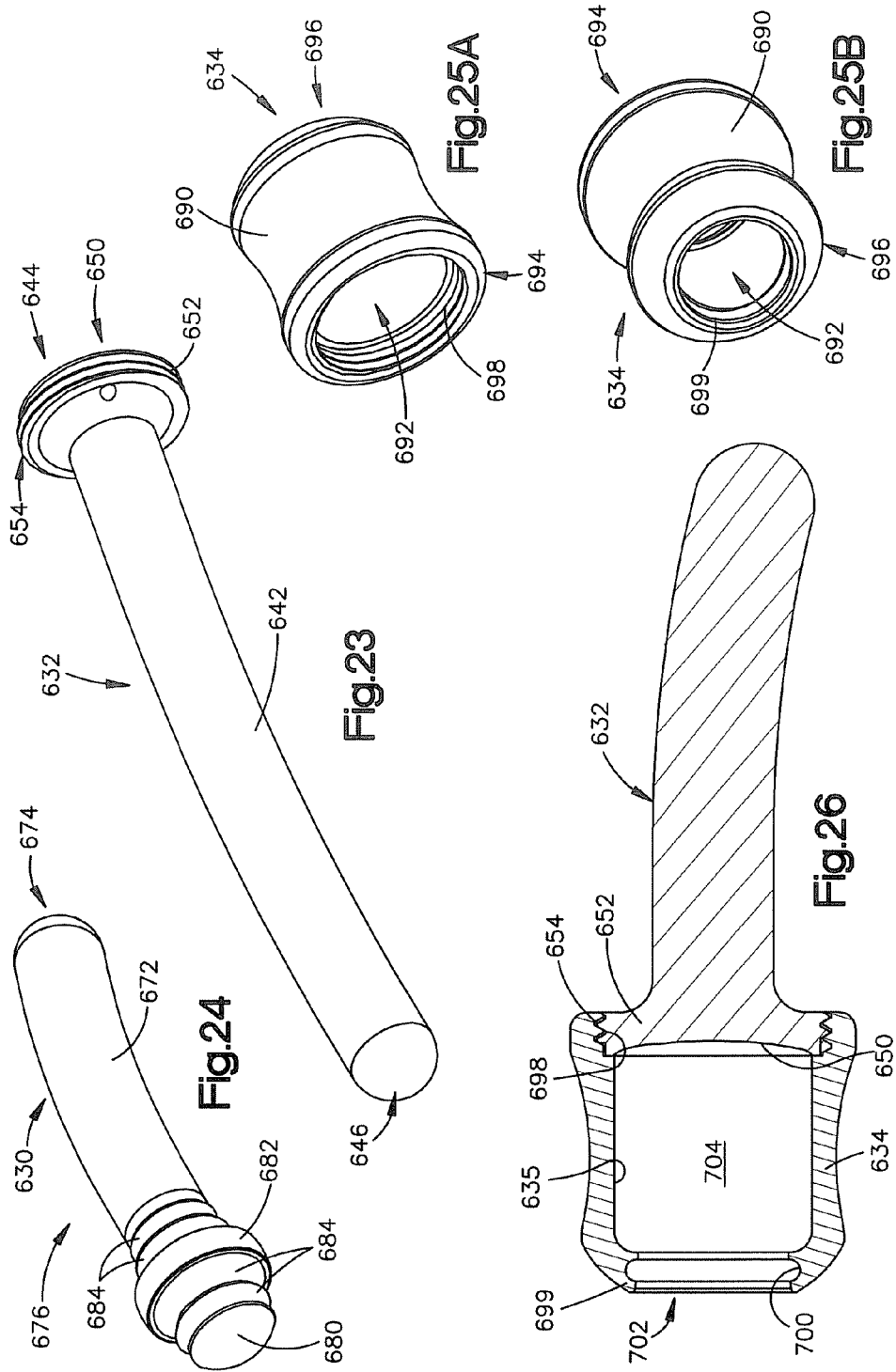

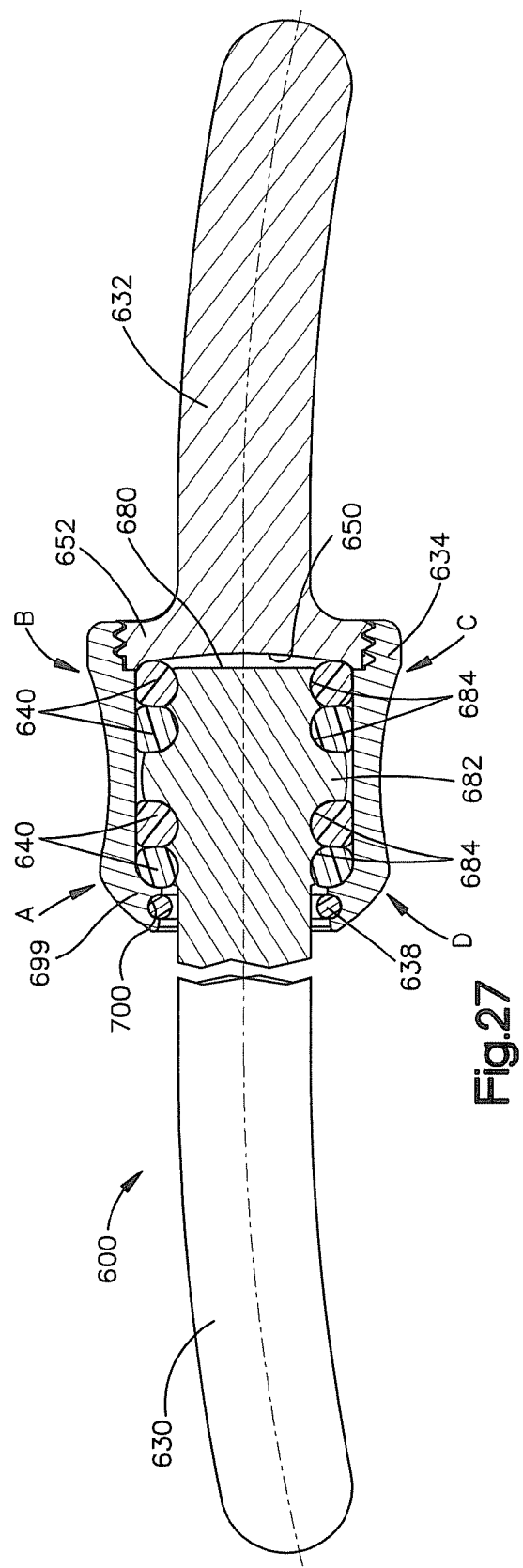

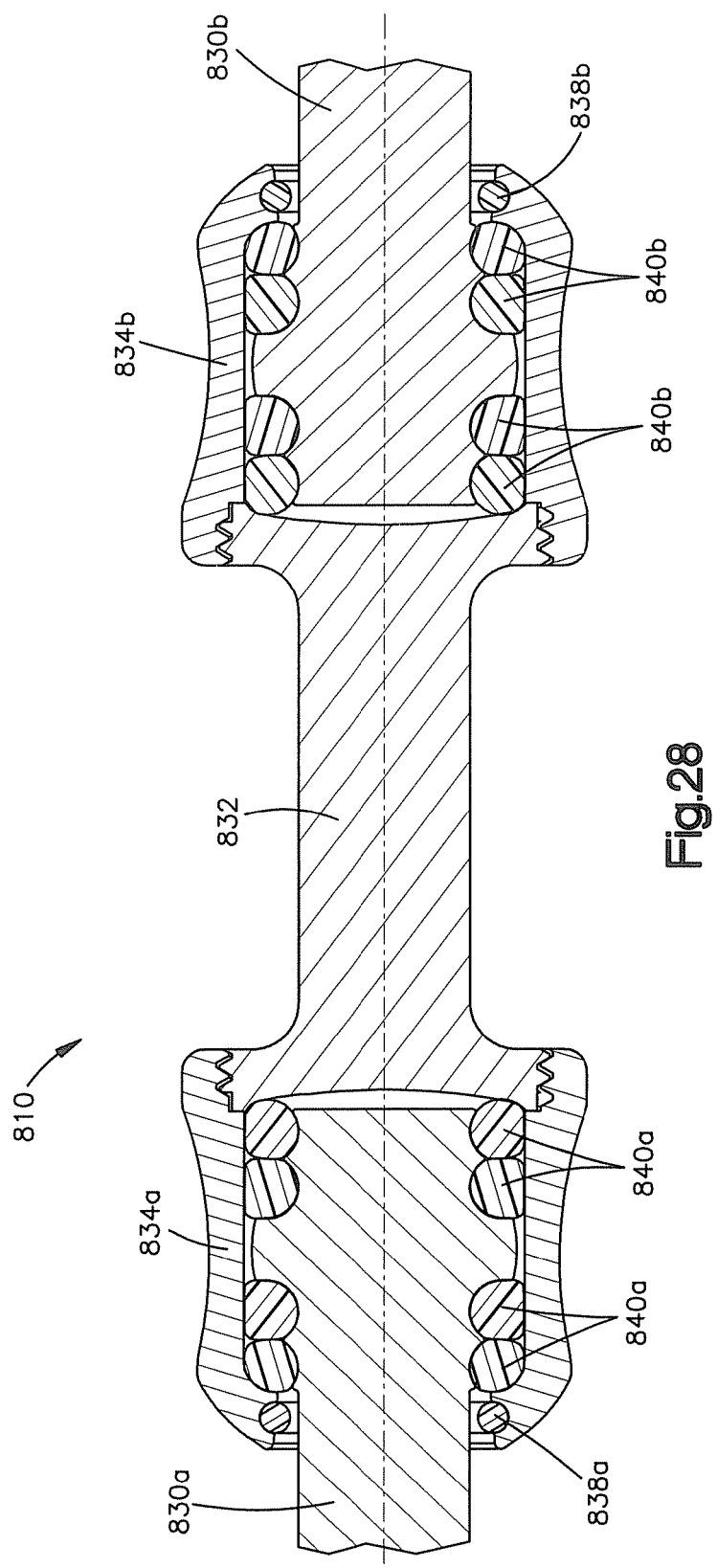

DYNAMIC STABILIZATION DEVICE

RELATED APPLICATIONS

This application claims the benefit of U.S. Provisional Patent Application Ser. No. 60/889,169 filed Feb. 9, 2007, for DYNAMIC STABILIZATION DEVICE, the entire disclosure of which is fully incorporated herein by reference.

BACKGROUND

A device or system may be implanted into a patient to control movement between two bones or tissue portions. For example, bone implants and systems are used for, among other purposes, control and stabilization of the posterior lumbar spine. In the case of spinal degeneration, for example, of a disc or a vertebra, the spine may be unstable, and undesired motion may be possible. In such a case, it is known to use a bone implant or system to stabilize the spine while still allowing some controlled motion.

Typical spinal systems include pedicle screws that attach to adjacent vertebrae; rigid or semi-rigid rods or plates that extend between the screws of adjacent vertebrae; and connectors for connecting the rods or plates with the screws. Some systems are designed not to allow for any relative movement between vertebrae. Other systems allow for some relative movement between vertebrae, such as via pivotal connectors and/or flexible rods or plates, in an attempt to allow some controlled movement of the spine while still stabilizing the spine.

SUMMARY

The present application is directed to an implantable, dynamic stabilization device. In one embodiment, the device includes a first member that is movably attached to a second member such that the first member may pivot, move axially, and/or rotate relative to the second member. The device may be used, for example, to extend between two bones in order to provide stabilization and motion preservation.

In one embodiment, the connection or joint between the first and second members are linked by a flexible joint. The joint may include one or more resilient or biasing element(s) to bias or dampen force when one member moves relative to the other. In another embodiment, the device includes a first elongated member having an end concentrically disposed in and retained within a housing portion that is attached to a second elongated member. A plurality of elastomeric elements are also disposed within the housing to provide resistance to relative movement between the elongated members.

In another embodiment, a flexible dynamic rod device is provided in which the stiffness of the rod and movement of the rod is customizable. In one embodiment, a plurality of resilient or biasing elements are associated with the connection or joint between a first and a second rod member. The number and stiffness of the resilient or biasing elements may be changed in order to customize the stiffness and the range of movement of the dynamic rod device.

The present application is also directed to a method of use for the device.

Further aspects and concepts will become apparent to those skilled in the art after considering the following description and appended claims in conjunction with the accompanying drawings.

BRIEF DESCRIPTION OF THE DRAWINGS

In the accompanying drawings, which are incorporated in and constitute a part of the specification, embodiments of the invention are illustrated, which, together with a general description given above, and the detailed description given below, serve to exemplify embodiments of the invention:

FIG. 3 is a perspective view of the embodiment of FIG. 2;

FIG. 4 is an exploded view of the embodiment of FIG. 3;

FIG. 5 is a perspective view of an embodiment of a first elongated member of the embodiment of FIG. 3;

FIG. 6 is a perspective view of an embodiment of a second elongated member of the embodiment of FIG. 3;

FIG. 7A is a perspective view of an embodiment of a housing portion of the embodiment of FIG. 3 illustrating a first end of the housing portion;

FIG. 7B is a perspective view of the housing of FIG. 7A illustrating a second end of the housing portion;

FIG. 8 is a cross section of the housing assembled to the first elongated member of the embodiment of FIG. 3.

FIG. 10 is a side view of the embodiment of FIG. 3 illustrating axial movement of the first elongated member relative to the second elongated member;

FIG. 11 is a side view of the embodiment of FIG. 3 illustrating pivotal movement of the first elongated member relative to the second elongated member;

FIG. 12 is a front view of the embodiment of FIG. 3 illustrating various directions of pivotal movement of the first elongated member;

FIG. 13 is a side view of the embodiment of FIG. 3 illustrating movement of the first elongated member during flexion and extension;

FIG. 14 is a perspective view of a third embodiment of a dynamic stabilization device as disclosed in the application;

FIG. 15 is an exploded view of the of the embodiment of FIG. 14;

FIG. 16 is a perspective view of an embodiment of a first elongated member of the embodiment of FIG. 14;

FIG. 17 is a cross-section view of the first elongated member of FIG. 16;

FIG. 18 is a perspective view of an embodiment of a second elongated member of the embodiment of FIG. 14;

FIG. 19 is a perspective view of an embodiment of a collar of the embodiment of FIG. 14;

FIG. 20 is a side cross-section view of the embodiment of FIG. 14;

FIG. 21 is a perspective view of a fourth embodiment of a dynamic stabilization device as disclosed in the application;

FIG. 22 is an exploded view of the of the embodiment of FIG. 21;

FIG. 23 is a perspective view of an embodiment of a first elongated member of the embodiment of FIG. 21;

FIG. 24 is a perspective view of an embodiment of a second elongated member of the embodiment of FIG. 21;

FIG. 25A is a perspective view of an embodiment of a housing portion of the embodiment of FIG. 21 illustrating a first end of the housing portion;

FIG. 25B is a perspective view of the housing of FIG. 25A illustrating a second end of the housing portion;

FIG. 26 is a cross section of the housing assembled to the first elongated member of the embodiment of FIG. 21; and FIG. 27 is a partial side cross-section view of the embodiment of FIG. 21; and FIG. 28 is a partial side cross-section view a fifth embodiment of a dynamic stabilization device as disclosed in the application.

DETAILED DESCRIPTION

The present application discloses an implantable, dynamic device used for controlling motion. Although the embodiments illustrate the use of the dynamic device in a spinal stabilization and motion preservation system, the device may be used to control the relative motion of a variety of structures and is not limited to spinal applications. For example, the device may be used to control the relative motion between bones and/or tissues in the body, such as the pelvis and the femur. While the embodiments illustrated and described herein are presented in the context of a segmented rod shaped implant device having a first cylindrical rod movably attached to a second cylindrical rod by a flexible joint that includes a housing and four elastomeric rings, those skilled in the art will readily appreciate that the present invention may be used and configured in other ways. For example, the first and second cylindrical rods may be configured in any suitable manner to connect between two bones or tissue portions. Thus, elongated members having configured other than cylindrical or rod-shaped may be used. For example, the cross-sectional configuration may be any suitable geometric shape. In addition, the movement of the first rod member relative to the second rod member may be axial, pivotal, and/or rotational and in one or more planes. Furthermore, the number and configuration of the resilient member(s) may vary and the composition need not be elastomeric. Any suitable resilient or biasing member(s) may be used at the connection between the first and second rod members. For example, more or less than four rings may be used, conventional springs or other biasing elements may be used, or the cavity or portions thereof may be filled with an energy absorbing material, such as for example a polymeric material.

The embodiments of the invention illustrate the use of the device in a spinal stabilization and motion preservation system that restricts certain types of motion in an otherwise abnormal or degenerative spine while allowing other types of motion so that the spinal segment is stabilized but not fused. Quantity of motion refers to the range of motion of the spine while quality of motion refers to the characteristics of a rotating vertebra, such as kinematics.

Figure 1:
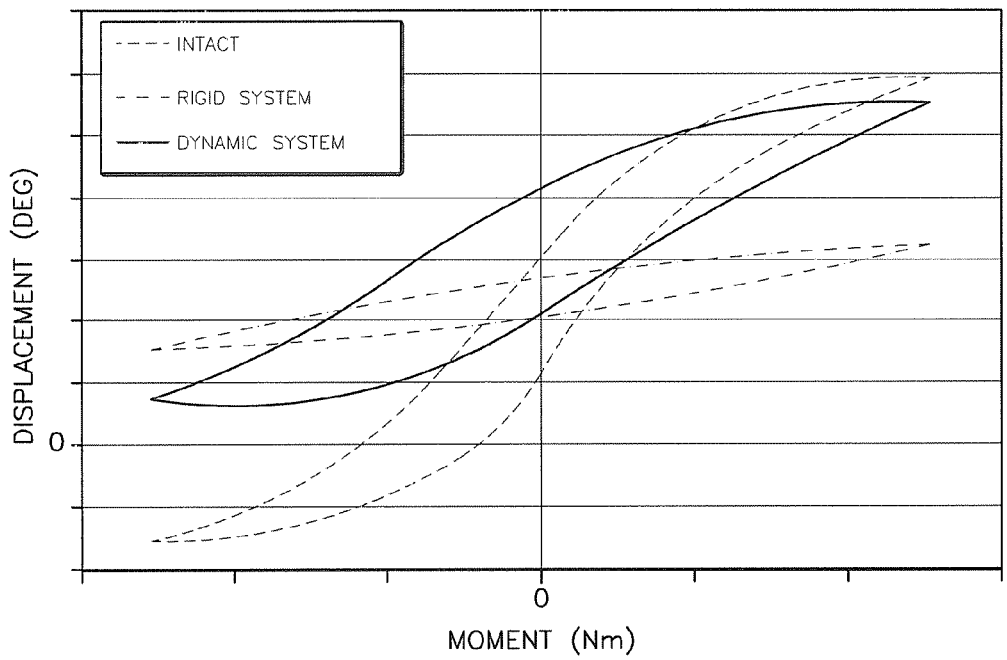
FIG. 1 is graph depicting the motion curves of an intact normal spine and an abnormal or degenerative spine outfitted with various types of rod/connector spinal stabilization systems.

For example, the graph shown in FIG. 1 depicts the motion curves of an intact normal spine and an abnormal or degenerative spine outfitted with either a rigid or dynamic spinal stabilization system. FIG. 1 illustrates that the use of a dynamic spinal stabilization system, for example a dynamic rod and dynamic connector such as the embodiments of the invention illustrated and described herein, allows for a more normal range of motion than the use of a conventional rigid spinal stabilization system.

The y-axis of the graph shown in FIG. 1 represents the displacement (degree of flexion/extension bending) and the x-axis represents the moment (Nm) acting on the vertebral junction. Positive moment values represent flexion (bending forward) while negative moment values represent extension (bending backward). Thus, the moment acting on the vertebral junction increases as a person bends forward (flexion) from a neutral position and decreases as the person returns to the neutral position. Similarly, the moment acting on the vertebral junction increases as a person bends backward (extension) from a neutral position and decreases as the person returns to the neutral position. The total range of motion may be calculated from the total displacement between the top and bottom of the motion curve.

As shown in the graph of FIG. 1, the range of motion of an abnormal or degenerative spine outfitted with a dynamic spinal stabilization system allows for almost as much flexion range of motion as a normal intact spine. Further, an abnormal or degenerative spine outfitted with a dynamic spinal stabilization system allows for an overall greater range of motion than an abnormal or degenerative spine outfitted with a rigid spinal stabilization system. As such, the use of a dynamic spinal stabilizations system, for example a dynamic rod and dynamic connector such as the embodiments of the invention illustrated and described herein, allows for a more normal quantity and quality of motion than the use of a conventional rigid spinal stabilization system.

While various aspects and concepts of the invention are described and illustrated herein as embodied in combination in the embodiments, these various aspects and concepts may be realized in many alternative embodiments, either individually or in various combinations and sub-combinations thereof. Unless expressly excluded herein all such combinations and sub-combinations are intended to be within the scope of the present invention. Still further, while various alternative embodiments as to the various aspects and features of the invention, such as alternative materials, structures, configurations, methods, devices, and so on may be described herein, such descriptions are not intended to be a complete or exhaustive list of available alternative embodiments, whether presently known or identified herein as conventional or standard or later developed. Those skilled in the art may readily adopt one or more of the aspects, concepts or features of the invention into additional embodiments within the scope of the present invention even if such embodiments are not expressly disclosed herein. Additionally, even though some features, concepts or aspects of the invention may be described herein as being a preferred arrangement or method, such description is not intended to suggest that such feature is required or necessary unless expressly so stated. Still further, or representative values and ranges may be included to assist in understanding the present invention however, such values and ranges are not to be construed in a limiting sense and are intended to be critical values or ranges only if so expressly stated.

It should be noted that for the purposes of this application, the terms attach (attached), connect (connected), and link (linked) are not limited to direct attachment, connection, or linking but also include indirect attachment, connection, or linking with intermediate parts, components, or assemblies being located between the two parts being attached, connected, or linked to one another. In addition, the terms attach (attached), connect (connected), and link (linked) may include two parts integrally formed or unitarily constructed.

It should also be noted that for the purposes of this application, the term implant (implantable, implanted, etc.) or surgical implant device is not limited to those devices implanted into a tissue or bone and completely covered by the skin, but also includes devices implanted into a tissue or bone and projecting through the skin.

Figure 1B:
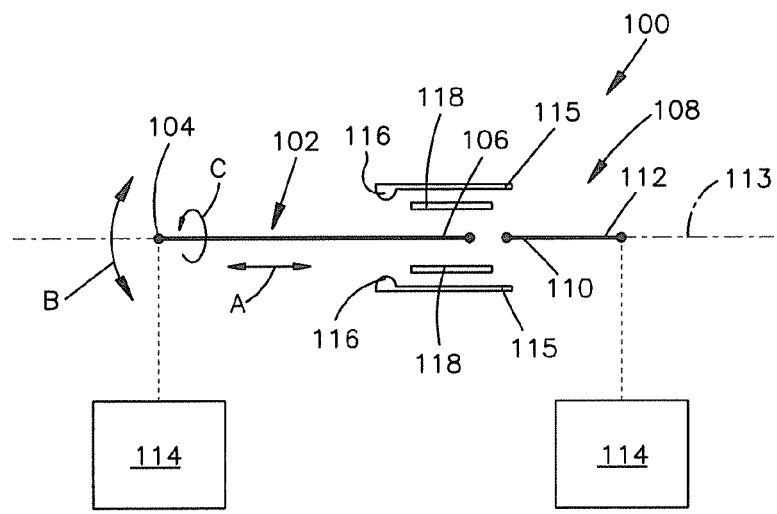
FIG. 1B is a schematic representation of a first embodiment of a dynamic stabilization device as disclosed in the application.

FIG. 1B illustrates a first embodiment of the implantable dynamic stabilization device 100. The device 100 includes a first elongated member 102 having a first end portion 104 and a second end portion 106 and a second elongated member 108 having a first end portion 110 and a second end portion 112. The second end portion 106 of the first elongated member 102 is positioned adjacent or proximate the position of the first end portion 110 of the second elongated member 108, such that the first elongated member and the second elongated member are generally aligned along an axis 113. The first end portion 104 of the first member 102 and the second end portion 112 of the second elongated member 108 are adapted to connect to other components 114 of motion stabilization and preservation system. Pedicle screws or some other osseous or tissue anchoring device is a non-limiting example of a component 114 to which the first and second members 102, 108 may connect to.

A housing portion 115 is associated with the first end portion 110 of the second elongated member 108. For example, the housing portion 115 may be a separate component attached to the first end portion 110 or may be formed integrally with the first end portion. The second end portion 106 of the first elongated member 102 is disposed within the housing portion 115 and is retained within the housing portion by a retaining portion 116, which may be any suitable retaining means that also permits the first elongated member 102 to be movable relative to the second elongated member 108. For example, the first elongated member 102 may move axially (shown by arrows A), pivotally (shown by arrows B), and rotationally about the axis 113 (shown by arrows C) relative to the second elongated member 108. One or more resilient members 118 may also be disposed within the housing portion 115 and oriented to provide an increasing resistance to relative axial and pivotal movement between the first and second elongated members 102, 108. For example, if a force is applied to move the first the first elongated member 102 axially away from or toward the second elongated member 108, and/or pivot away from the axis 113, the one or more resilient members 118 will resist the movement. The farther the first elongated member moves from an initial neutral or unloaded position, the more resistance the resilient members provide. In addition, once the force is removed or sufficiently reduced, the resilient members will bias the first elongated member back to the neutral or unloaded position.

The resilient members 118 may also be positioned within the housing portion 115 in a manner that prevents the first elongated member 102 from contacting the inner surface of the housing when the first elongated member moves relative to the second elongated member 108.

Thus, the housing portion 115, the retaining means 116, and the resilient members 118 cooperate to form a flexible joint or coupling between the first elongated member 102 and the second elongated member 108 that allows for quality of motion between the members.

The resilient members 118 and/or other structure associated with the flexible coupling, may also provide limits to the amount of movement allowed between the first and second members 102, 108. For example, a stop surface or bump stops (not shown) may be included on the device that impede further relative movement of one member relative to the other member. The stop surface or bump stops may include a resilient material that provides resistance to pivotal movement of the first elongated member that increases the farther the first elongated member pivots relative to the second elongated member. The stop surface or bump stop may eventually provide a hard stop that prevents the first elongated member from pivoting beyond a certain amount.

Figure 2:
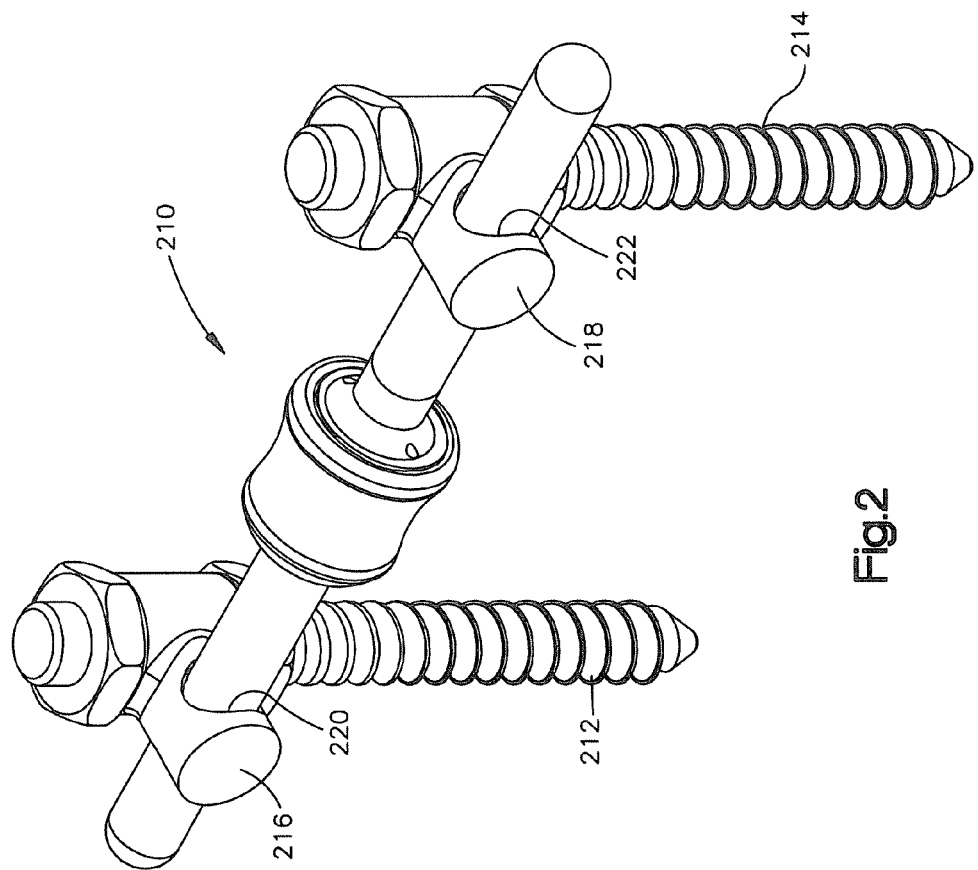
FIG. 2 is a perspective view of a second embodiment of a dynamic stabilization device as disclosed in the application, illustrated connected to a pair of bone screws.

FIG. 2-13 illustrate a second embodiment of an implantable, dynamic stabilization device 210. Referring to FIG. 2, the dynamic stabilization device 210 is installed between a pair of components 212, 214 of a stabilization and motion preservation system. The device 210 may be installed between a variety of system components. Any system components in which controlled motion between the components is desirable may be used. In the depicted embodiment, the components 212, 214 are bone anchoring elements realized as pedicle screws. The dynamic device 210 connects to each of the pedicle screws 212, 214. The dynamic device 210 may attach to the pedicle screws in any suitable manner. In the depicted embodiment, each of the screws 212, 214 includes a boss portion 216, 218 having a through bore 220, 222. The device 210 is inserted through each of the through bores 220, 222 and secured in place by any suitable means, such as for example by set-screws or pins. The connection between the device 210 and each of the screws 212, 214 may be fixed or may be flexible. For example, pivotal connections between a support rod and bone screws in stabilization and motion preservation systems are known. The device 210 may be used with known or newly developed pivotal or flexible connections.

Referring to FIGS. 3 and 4, the depicted embodiment of the device 210 includes a first elongated member 230 movably attached to a second elongated member 232. The first and second members 230, 232 may be configured in a variety of ways. Any members capable of being movably attached to each other while also being attached to other system components to provide controlled movement between the components may be used. In the depicted embodiment, the first elongated member 230 is realized as a first rigid rod and the second elongated member 232 is realized as a second rigid rod attached to the first rigid rod by a housing 234. The device 210 also includes one or more stop surfaces or bump stops 238 and one or more resilient members 240 (see FIG. 4). In the depicted embodiment, the one or more bump stops 238 and the one or more resilient members 240 are realized as generally angular or doughnut-shaped components, but other shapes and other configurations are possible.

Referring to FIG. 5, the second elongated member 232 includes an elongated, generally cylindrical body 242. The body 242 has a first end portion 244 and a second end portion 246. The second end portion 246 is adapted to connect or attach to another system component, such as for example a pedicle screw. The first end portion 244 is adapted to connect to the housing 234. The first end portion 244 includes an end face 250 and a flange 252 that extends radially from the second elongated member 232. The flange 252 includes male threads 254 disposed on an outer edge. The male threads 254 are configured to threadably mate with the housing 234 (see FIG. 8). The second elongated member 232 and the housing 234, however, may be configured to attach by any suitable means.

Referring to FIG. 6, the first elongated member 230 includes an elongated, generally cylindrical body 272. The body 272 has a first end portion 274 and a second end portion 276. The first end portion 274 is adapted to connect or attach to another system component, such as for example a pedicle screw.

The second end portion 276 is adapted to be received within the housing 234. The second end portion 276 includes an end face 280 and a flange 282 that extends radially from the first elongated member 230. In the depicted embodiment, a plurality of circumferential grooves 284 are disposed adjacent to the flange 282. The grooves 284 are adapted to receive the resilient members 240. In the illustrated embodiment, two grooves 284 are located on either side of the flange 282, each groove being adapted to receive one resilient member 240. In other embodiments, however, the number, configuration, and position of the grooves may vary. For example, the first elongated member 230 may not include any grooves or may include more or less than two grooves on each side of the flange 282. Furthermore, the number of grooves on one side of the flange 282 may differ from the number of grooves on the other side and/or more than one resilient member may be received by a single groove.

FIGS. 7A and 7B illustrate the housing 234. The housing 234 may be configured in a variety of ways. Any structure capable of connecting the second elongated member 232 and receiving a portion of the first elongated member to form a flexible joint may be used. In the depicted embodiment, the housing 234 has a generally cylindrical body 290 that forms a through bore 292. The body 290 has a first end portion 294 and a second end portion 296. The first end 294 includes female threads 298 for threadably mating with the male threads 254 on the second elongated member 232. In other embodiments, however, the housing 234 and the second elongated member 232 may attach by any suitable means. The second end portion 296 includes an inwardly radially extending shoulder 299 having a circumferential groove 300 (see FIG. 8). The shoulder 299 forms an opening 302 at the second end portion 296 (see FIG. 8). The opening 302 may be circular or any other suitable shape.

Figure 9:
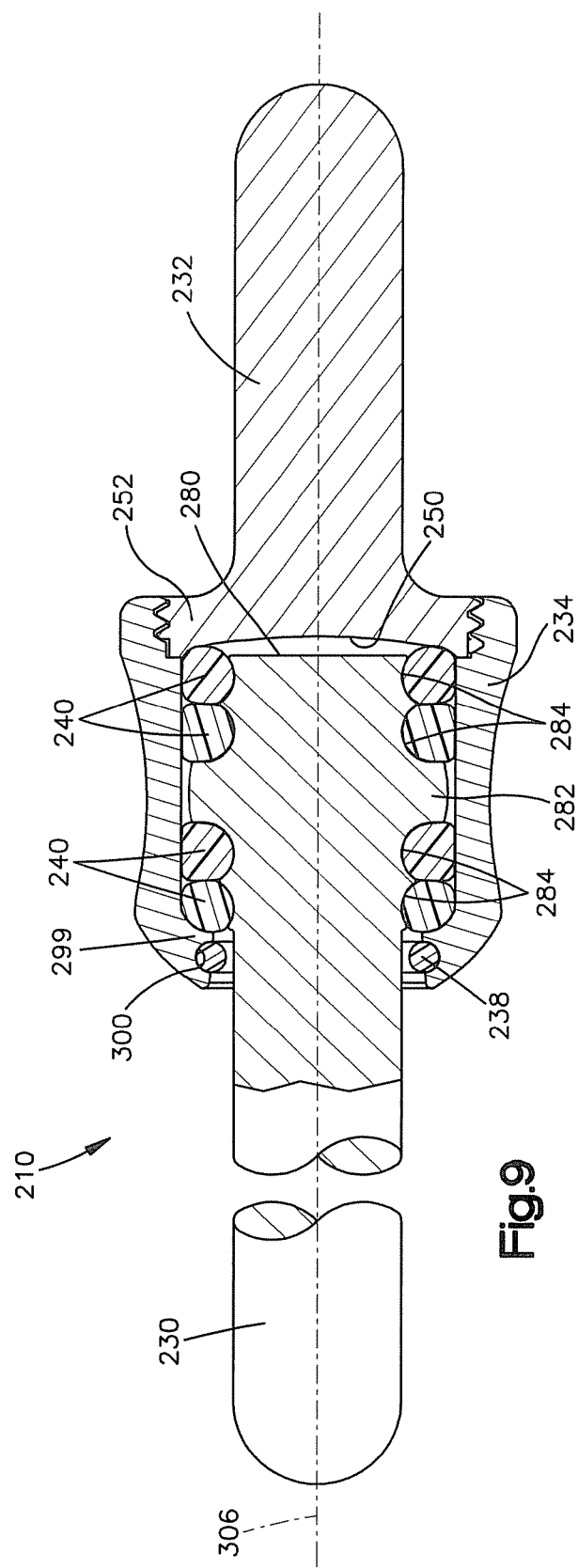
FIG. 9 is a side cross-section view of the embodiment of FIG. 3.

Referring to FIGS. 8-9, when assembled, the second elongated member 232 and the inner surface 235 of the housing 234 form a cavity 304 (FIG. 8). The second end portion 276 of the first elongated member 230 is disposed within the cavity 304 such that the body 272 of the first elongated member 230 extends from the cavity 304, via the opening 302, generally along an axis 306. In a neutral, unloaded, or free state, the first elongated member 230 and the second elongated member 232 are generally aligned along the axis 306, as shown in FIG. 9.

The four annular, resilient members 240 are disposed within the cavity 304. In the depicted embodiment, the resilient members 240 may be formed from or include a variety of resilient materials that are suitable for mammalian implantation, such as for example, but not limited to, polyethylene or polyurethane.

The resilient members 240 have an outer diameter that is slightly smaller than the diameter of the inner surface 235. The inner diameter of the resilient members 240 is slightly smaller that than the diameter of the first member 230 such that the resilient members are stretched in order for the member's inner diameter to fit onto the first member. In other embodiments, however, the inner diameter of the resilient members 240 may be the same as or slightly larger that the diameter of the first member 230. As depicted, two resilient members 240 are positioned within grooves 284 between the flange 282 and the end face 280 of the first elongated member 230 and two resilient members 240 are positioned within grooves 284 between the flange 282 and the inward extending shoulder 299 of the housing 234. The flange 282 has a diameter that is smaller than the diameter of the inner surface 235 but larger than the inner diameter of the resilient members 240, such that the flange separates the resilient members within the cavity 304. Furthermore, the diameter of the flange 282 is also larger than the diameter of the opening 302 formed by the shoulder 299. Thus, the shoulder 299 acts as a retaining portion to retain the second end portion 276 of the first elongated member 230 within the cavity 304 between the end face 250 of the second elongated member 232 and the shoulder 299.

Referring to FIG. 9, the generally annular bump stop 238 is adapted to be received within the groove 300 of the shoulder 299. The bump stop 238 may be held within the groove 300 by any suitable means, such as but not limited to, interference or friction fit, adhesives, or the resiliency of the bump stop itself. The bump stop 238 provides a specific travel limit for pivotal movement of the first elongated member 230 relative to the second elongated member 232. The bump stop 238 may be configured in a variety of ways. Any structure capable of limiting the motion of the first elongated member 230 relative to the second elongated member 232 may be used. For example, though the bump stop 238 is depicted as a single, continuous annular component, the bump stop 238 may be non-continuous (e.g. have a gap) or may be configured as multiple pieces. Furthermore, the bump stop 238 may be formed from any suitable material. Thus, the bump stop 238 may be formed from a hard material, such as stainless steel, for example, or may be formed with at least a portion designed to dampen or cushion movement while providing a limit to travel. For example, the bump stop 238 may be formed from or include a resilient material such as an elastomer or some other dampening material such as silicon. The bump stop 238 provides resistance to pivotal movement of the first elongated member 230 that increases the farther the first elongated member pivots relative to the second elongated member 232. Thus, the bump stop 238 may provide a nonlinear response.

Referring to FIGS. 10 and 12, the first elongated member 230 is movably attached to the second elongated member 232. Movement of the first elongated member 230 relative to the second elongated member 232 may be controlled and constrained by one or more of: the cavity 304, the shoulder 299 of the housing 234, the size and shape of the opening 302, the configuration of the bump stop 238, and the resilient members 240. Furthermore, the resilient members 240 are positioned within the housing in a manner that prevents the first elongated member 230 from directly contacting the inner surface of the housing 234 as the first elongated member moves relative to the second elongated member 232.

As illustrated in FIG. 10, the first elongated member 230 is movable axially relative to the second elongated member 232. In a free, neutral, or unloaded state, as shown by solid lines, the first elongated member 230 is in a first position X. If an axially compressive force is applied between the first and second elongated members 230, 232, the first elongated member moves axially toward the second elongated member toward a second position Y. This axial compression results in compression of the resilient members 240 disposed between the flange 282 and the end face 250 (FIG. 9). When compressing, the resilient members 240 resist the movement by imparting a bias force against the flange 282. The more the resilient members 240 are compressed, the greater the bias force. In addition, once the compression force is removed or sufficiently decreased, the compressed resilient members 240 return to their natural, free state shape; thus imparting a return force onto the flange 282.

If an axially distracting force is applied between the first elongated member 230 and second elongated member 232, the first elongated member moves axially away from the second elongated member toward a third position Z. This axial distraction results in compression of the resilient members 240 disposed between the flange 282 and a shoulder 299. When compressing, the resilient members 240 resist the movement by imparting a bias force against the flange 282. The more the resilient members 240 are compressed, the greater the bias force. In addition, once the distraction force is removed or sufficiently decreased, the compressed resilient members 240 will return to their free state shape; thus imparting a return force onto the flange 282.

The amount of compression and distraction of the device 210 may be customized by changing the number, configuration, and/or material of the resilient members. For example, the device 210 may allow for several millimeters of distraction. However, this amount may be modified by changing the type of, configuration of, or number of resilient members 240 between the flange 282 and the shoulder 299. In this way, the amount of distraction allowed may be different or the same as the amount of compression allowed.

As illustrated in FIG. 11, the first elongated member 230 may also pivot relative to the second elongated member 232. The direction and amount of pivotal movement may depend on one or more of: the size and shape of the opening 302, the size, shape, and material of the bump stop 238, and the number, configuration, and material of the resilient members 240. For example, if the opening 302 is elliptical, the first elongated member 230 will have a greater range of pivotal movement along the major axis of the elliptical bore than along the minor axis of the elliptical bore. As shown in FIG. 12, however, a circular shape of the opening 302 allows the first elongated member 230 to pivot relative to the second elongated member 232 in all directions. Thus, the first elongated member 230 is capable of pivoting relative to the second elongated member 232 about a plurality of pivot axes. For example, pivot axis 291 illustrated the axis that the first elongated member 230 pivots about when the first elongated member moves in a direction illustrated by arrows B while pivot axis 293 illustrated the axis that the first elongated member pivots about when the first elongated member moves in a direction illustrated by arrows A.

When the first elongated member 230 pivots relative to the second elongated member 232, the bump stop 238 act to limit the amount of pivotal movement of the first elongated member by interfering with the movement. In addition, some of the resilient members 240 within the housing 234 may also be compressed as a result of pivotal movement of the first elongated member 230. The bump stop 238 and resilient members 240 may not only limit the pivotal movement of the first elongated member 230, but also provide a softening or transition region where movement is restricted. For example, the bump stop 238 and resilient members 240 may provide a hard stop at three to five degrees from the axis 306, but gradually increase the stiffness of the connection or joint leading up to the hard stop.

In one embodiment, the device 210 may allow for three to five degrees of pivotal movement. If a different amount of movement is desired, different spring elements or bump stop 238 (size, shape, material, etc.) or a different sized or shaped opening 302 may be used. The first elongated member 230 may also rotate relative to the second elongated member 232. The first elongated member 230 may rotate within the housing 234 and about the axis 306. In certain embodiments, the resilient members 240 may provide frictional resistance to the rotation.

Referring to FIGS. 9 and 13, the first elongated member 230 may both pivot and distract or compress relative to the second elongated member 232. When used in an implantable spinal stabilization system in which the device 210 is attached at either end to bone anchoring members, which are attached to vertebrae, the device may be configured to provide controlled flexion and extension of the spine, along with limited lateral bending and rotation. For example, as shown in FIG. 13, when the spine is flexed, the first elongated member 230 will pivot and distract relative to the second elongated member 232. Accordingly, when the spine is extended, the first elongated member 230 will pivot and compress relative to the second elongated member 232. The combined pivotal movement and axial movement is consistent with the relative movement between vertebra; thus, the device may effectively provide controlled movement in the spinal stabilization system.

As previously indicated, the resilient members 240 provide an increasing resistance to movement the more the first elongated member 230 pivots or moves axially relative to the second elongated member 232. This resistance is created by compressing the resilient members 240. Thus, the more the resilient members 240 are compressed, the more the members resists further compression. In some instances, especially when both pivotal and axial movement occur, the amount of compressive force and the direction of the compression forces acting on the resilient members 240 varies between the resilient members as well as across a single resilient member.

To illustrate, the four corners within the housing 234 are identified in FIG. 9 as A, B, C, and D. In the neutral position, as shown in FIG. 9, the resilient members 240 may be compressed to some degree, thus, movement of the first elongated member 230 relative to the second elongated member 232 increases or decreases the compressive stress on the resilient members 240 or portions thereof. When the first elongated member 230 pivots and distracts relative to the second elongated member (i.e. the position labeled in FIG. 13 as "flexion"), the portions of the resilient members 240 in each corner experience different compressive forces. For example, the portions of the resilient members 240 in corner A are further compressed both axially by the flange 282 moving toward the radially extending shoulder 299 and radially by the grooves 284 as the first elongated member 230 pivots toward the corner A. Conversely, the portions of the resilient members 240 in corner B are less compressed both axially and radially as the flange moves axially away from the corner B and the first elongated member pivots away from the corner B. In a similar manner, the portions of the resilient members 240 in corner C are more compressed radially and less compressed axially and the portions of the resilient members 240 in corner D are more compressed axially and less compressed radially.

In the depicted embodiment, movement of the of the first elongated member 230 relative to the second elongated member 232 generally results in compression of the resilient members without axially movement of the resilient members. Thus, the resistance to movement is generally achieved by physical, cross-sectional deformation of the resilient members 240 without axial displacement of the resilient members. Further, compression of the resilient members 240 may occur both axially and radially with different portions of the resilient members 240 experiences different compressive forces, both in magnitude and direction.

Referring to FIGS. 14 and 15, the depicted embodiment of the device 410 includes a first elongated member 430 movably attached to a second elongated member 432. The first and second members 430, 432 may be configured in a variety of ways. Any members capable of being movably connected to each other while also being connected for movement with other system components to provide controlled movement between the components may be used. In the depicted embodiment, the first elongated member 430 is realized as a first rigid rod and the second elongated member 432 is realized as a second rigid rod attached to the first member by a collar 434. The first and second members 430, 432 are depicted as solid rods, however, the members could be formed as tubes or other suitable configurations. The device 410 also includes a retaining device 436, such as a C-clip for example, for securing the collar 434 to the second member 432, one or more bump stops 438, and one or more resilient members 440. In the embodiment of FIG. 15, the resilient members 440 are depicted as generally annular or doughnut-shaped but other shapes and configurations are possible.

Referring to FIGS. 16 and 17, the second elongated member 432 includes a first generally cylindrical end portion forming a housing 442 with a first terminal end 443 and a second generally cylindrical end portion 444 having a second terminal end 445. The housing 442 in the depicted embodiment is formed integrally with the second member 432. In other embodiments, however, the housing 442 may be formed as a separate component that attaches to the second member 432. The diameter of the second generally cylindrical end portion 444 is smaller than the diameter of the housing 442. The second end portion 444 is adapted to connect to another system component, such as for example a pedicle screw, while the housing 442 is adapted to connect to the first elongated member 430. The housing 442 forms an opening 446 circumscribed by a lip 448. The opening 446 opens to a cavity 450 (FIG. 17) having generally cylindrical side walls 452 and an end wall 454. The side walls 452 have generally parallel inner and outer side surfaces 456, 458. The housing 442 also includes a circumferential groove 460 along the inner side surface 456 proximate the opening 446.

Referring to FIG. 18, the first elongated member 430 includes a first generally cylindrical end portion 462 having a first terminal end 464 and a second generally cylindrical end portion 466 having a second terminal end 468. The first end portion 462 is adapted to connect to a component of a spinal stabilization system 414, such as a pedicle screw for example, while the second end portion 466 is adapted to be received within the cavity 450 for connecting to the second elongated member 432. The second end portion 466 includes a radially extending flange 470 proximate the second terminal end 468.

Referring to FIGS. 15 and 19, the collar 434 includes a first generally cylindrical end 472 and a second generally cylindrical end 474 having a diameter smaller than the diameter of the first generally cylindrical end 472. The second end 474 is connected to the first end 472 by a radially extending shoulder 476 and the second end 474 includes a circumferential groove 478. The collar 434 includes a through bore 480 (FIG. 19). In the depicted embodiment, the through bore 480 is generally oval or elliptical shaped, though other shapes and configurations are possible.

Referring to FIG. 20, when assembled, the second end 466 of the first elongated member 430 is received within the cavity 450 of the housing 442 of the second elongated member 432 along an axis 482. Four annular resilient members 440 are disposed within the cavity 450. In the embodiment, the resilient members 440 may be formed from or include a variety of materials that are suitable for mammalian implantation, such as for example, but not limited to, polyethylene or polyurethane.

The resilient members 440 have an outer diameter that is slightly smaller than the inner diameter of the cavity 450. The inner diameter of the resilient members 440 is slightly smaller that than the diameter of the first member 430 such that the resilient members are stretched in order for the member's inner diameter to fit onto the first member. In other embodiments, however, the inner diameter of the resilient members 440 may be the same as or slightly larger that the diameter of the first member 430. As depicted, two resilient members 440 are positioned between the flange 470 and the cavity end wall 454 and two resilient members 440 are positioned between the flange 470 and the collar 434. The flange 470 has a diameter that is smaller than the diameter of the cavity 450 and larger than the inner diameter of the resilient members 440 such that the flange separates the members within the cavity 450.

The first elongated member 430 is received through the through bore 480 in the collar 434, such that the collar is positioned between the flange 470 and the first terminal end 464. The flange 470 has an outer diameter that is too large to fit through the bore 480, thus the collar functions as a retaining device or portion that retains the second end 468 of the first elongated member 430 within the cavity 450.

The collar 434 attaches to the second elongated member 432 to retain the second end portion 466 of the first elongated member 430 and the resilient members 440 within the cavity 450. The second end of the collar 434 may have a diameter that is smaller than the inner diameter of the cavity 450 proximate the lip 448. When installed, the second end 474 of the collar 434 is received within the cavity 450 such that the shoulder 476 on the collar abuts the lip 448. In this position, the circumferential groove 478 on the collar 434 and the circumferential groove 460 on the side wall 452 of the housing 442 of the second elongated member 432 are radially aligned. A retaining means 436, realized as a C-clip for example, may be disposed within both of the grooves 460, 478 to retain the collar 434 in position. The collar 434, however, may be retained in position by any suitable means. Thus, the second end 474 of the collar 434 may act as a stop to retain the second end 466 of the first elongated member 430 and the resilient members 440 within the cavity 450.

Referring to FIGS. 15 and 20, one or more bump stops 438 may be installed on the inner surface of the bore 480. For example, in the depicted embodiment, a pair of crescent-shaped bump stops 438 are installed in the bore 480. However, a single bump stop, more than two bump stops, or no bump stops may be used. In addition, other configurations for the bump stops are possible. Any structure capable of providing a hard limit to relative motion between the elongated members 430, 432 may be used. In the depicted embodiment, at least a portion of the bump stops 438 are made from a viscoelastomeric material, thus they provide an increasing resistance to relative motion over a given range until the relative motion reaches a limit at which point the bump stops provide a hard stop.

In operation, the device 400 functions in generally the same manner as described in relation to the embodiment of FIGS. 2-14. Thus, the device 400 allows for the first elongated member 430 to move axially, pivotally, and rotationally relative to the second elongated member 432. Movement of the first elongated member 430 may be constrained by one or more of: the cavity side wall 452, the second end portion 474 of the collar 434, the size and shape of the collar bore 480, one or more bump stops 438, and the resilient members 440. Furthermore, the resilient members 440 are positioned within the housing in a manner that prevents the first elongated member 430 from directly contacting the side wall 452 of the or the end wall 454 as the first elongated member moves relative to the second elongated member 432.

When a force is applied to the first or second elongated member 430, 432, the members may move axially, pivotally, rotationally, or all three, relative to each other away from the neutral position. As a result, one or more of the resilient members 440 will be compressed between the flange 470 and the second end 474 of the collar 434 (distraction) and/or between the flange and the end wall 454 and resist the relative movement. The farther the elongated members 430, 432 compress, distract, or pivot from the neutral position, the more resistance the resilient members 440 provide. The configuration of the device 400, such as for example, the size of the cavity 450, the size of the flange 470, the number, size, and material of the resilient members 440, the shape and size of the bore 480, and size, shape, and material of the bump stops 438, will limit the amount of axially and pivotal movement that may occur between the first and second elongated members 430, 432. When the force being applied is removed or sufficiently reduced, the resilient members 440 will bias the elongated members 430, 432 back to the neutral position.

FIGS. 21-27 illustrate a fourth embodiment of a dynamic stabilization device 610. Referring to FIGS. 21 and 22, the depicted embodiment of the device 610 includes a first elongated member 630 movably attached to a second elongated member 632. The first and second members 630, 632 may be configured in a variety of ways. Any members capable of being movably attached to each other while also being attached to other system components to provide controlled movement between the components may be used. In the depicted embodiment, the first elongated member 630 is realized as a first rigid rod and the second elongated member 632 is realized as a second rigid rod attached to the first rod by a housing portion 634. The device 610 also includes one or more bump stops 638 and one or more resilient members 640 (see FIG. 22). In the depicted embodiment, the one or more bump stops 638 and the one or more resilient members 640 are realized as generally annular or doughnut-shaped components, but other shapes and other configurations are possible.

Referring to FIG. 23, the second elongated member 632 includes an elongated, generally cylindrical body 642 that is slightly curved or angled. The body 642 has a first end portion 644 and a second end portion 646. The second end portion 646 is adapted to connect or attach to another system component, such as for example a pedicle screw. The first end portion 644 is adapted to connect to the housing 634. The first end portion 644 includes an end face 650 and a flange 652 that extends radially from the second elongated member 632. The flange 652 includes male threads 654 disposed on an outer edge. The male threads 654 are configured to threadably mate with the housing 634 (see FIG. 26). The second elongated member 632 and the housing 634, however, may be configured to attach by any suitable means.

Referring to FIG. 24, the first elongated member 630 includes an elongated, generally cylindrical body 672 that is slightly curved or angled. The body 672 has a first end portion 674 and a second end portion 676. The first end portion 674 is adapted to connect or attach to another system component, such as for example a pedicle screw.

The second end portion 676 is adapted to be received within the housing 634. The second end portion 676 includes an end face 680 and a flange 682 that extends radially from the first elongated member 630. In the depicted embodiment, a plurality of circumferential grooves 684 are disposed adjacent to the flange 682. The grooves 684 are adapted to receive the resilient members 640. In the illustrated embodiment, two grooves 684 are located on either side of the flange 682, each groove being adapted to receive one resilient member 640. In other embodiments, however, the number, configuration, and position of the grooves may vary. For example, the first elongated member 630 may not include any grooves or may include more or less than two grooves on each side of the flange 682. Furthermore, the number of grooves on one side of the flange 682 may differ from the number of grooves on the other side and/or more than one resilient member may be received by a single groove.

FIGS. 25A and 25B illustrate the housing portion 634. The housing portion 634 may be configured in a variety of ways. Any stricture capable of connecting the second elongated member 632 and receiving a portion of the first elongated member to form a flexible joint may be used. In the depicted embodiment, the housing portion 634 has a generally cylindrical body 690 that forms a through bore 692. The body 690 has a first end portion 694 and a second end portion 696. The first end portion 694 includes female threads 698 for threadably mating with the male threads 654 on the second elongated member 632. In other embodiments, however, the housing portion 634 and the second elongated member 632 may attach by any suitable means. The second end portion 696 includes an inwardly radially extending shoulder 699 having a circumferential groove 700 (see FIG. 26). The shoulder 699 forms an opening 702 at the second end portion 696 (see FIG. 26). The opening 702 may be circular or any other suitable shape.

Referring to FIGS. 26-27, when assembled, the end face 650 of the second elongated member 632 and the housing portion 634 form a cavity 704 (FIG. 26). The second end portion 676 of the first elongated member 630 is disposed within the cavity 704 such that the body 672 of the first elongated member 630 extends from the cavity 704, via the opening 702.

The four annular, resilient members 640 are disposed within the cavity 704. In the depicted embodiment, the resilient members 640 may be formed from or include a variety of resilient materials that are suitable for mammalian implantation, such as for example, but not limited to, polyethylene or polyurethane.

The resilient members 640 have an outer diameter that is slightly smaller than the diameter of the inner surface 635. The inner diameter of the resilient members 640 is slightly smaller that than the diameter of the first member 630 such that the resilient members are stretched in order for the member's inner diameter to fit onto the first member. In other embodiments, however, the inner diameter of the resilient members 640 may be the same as or slightly larger that the diameter of the first member 630. As depicted, two resilient members 640 are positioned within grooves 684 between the flange 682 and the end face 680 of the first elongated member 630 and two resilient members 640 are positioned within grooves 684 between the flange 682 and the inward extending shoulder 699 of the housing portion 634. The flange 682 has a diameter that is smaller than the diameter of the inner surface 635 but larger than the inner diameter of the resilient members 640, such that the flange separates the resilient members within the cavity 704. Furthermore, the diameter of the flange 682 is also larger than the diameter of the opening 702 formed by the shoulder 699. Thus, the shoulder 699 acts as a retaining portion to retain the second end portion 676 of the first elongated member 630 within the cavity 704 between the end face 650 of the second elongated member 632 and the shoulder.

Referring to FIG. 27, the generally annular bump stop 638 is adapted to be received within the groove 700 of the shoulder 699. The bump stop 638 provides a specific travel limit for pivotal movement of the first elongated member 630 relative to the second elongated member 632. The bump stop 638 may be configured in a variety of ways. Any structure capable of limiting the motion of the first elongated member 630 relative to the second elongated member 632 may be used. For example, though the bump stop 638 is depicted as a single, continuous annular component, the bump stop 638 may be non-continuous (e.g. have a gap) or may be configured as multiple pieces. Furthermore, the bump stop 638 may be formed from any suitable material. Thus, the bump stop 638 may be formed from a hard material, such as stainless steel, for example, or may be formed with at least a portion designed to dampen or cushion movement while providing a limit to travel. For example, the bump stop 638 may be formed from or include a resilient material such as an elastomer or other dampening material such as silicon. The resilient bump stop 638 provides resistance to pivotal movement of the first elongated member 630 that increases the farther the first elongated member pivots relative to the second elongated member 632. Thus, the bump stop 638 may provide a nonlinear response.

In operation, the device 610 functions in generally the same manner as described in relation to the embodiment of FIGS. 2-13. Thus, the device 610 allows for the first elongated member 630 to move axially, pivotally, and rotationally relative to the second elongated member 632. Movement of the first elongated member 630 relative to the second elongated member 632 may be controlled and constrained by one or more of: the cavity 704, the shoulder 699 of the housing 634, the size and shape of the opening 702, the configuration of the bump stop 638, and the resilient members 640. Furthermore, the resilient members 640 are positioned within the housing in a manner that prevents the first elongated member 630 from directly contacting the inner surface of the housing 634 as the first elongated member moves relative to the second elongated member 632.

When a force is applied to the first or second elongated member 630, 632, the members may move axially, pivotally, or both, relative to each other away from the neutral position. As a result, one or more of the resilient members 640 will be compressed between the flange 682 and the shoulder 699 (distraction) and/or between the flange and the end face 650 and resist the relative movement. The farther the elongated members 630, 632 compress, distract, or pivot from the neutral position, the more resistance the resilient members 640 provide. The configuration of the device 610, such as for example, the size of the cavity 704, the size of the flange 682, the number, size, and material of the resilient members 640, the size of the opening 702, and size, shape, and material of the bump stop 638, will limit the amount of axially and pivotal movement that may occur between the first and second elongated members 630, 632. When the force being applied is removed or sufficiently reduced, the resilient members 640 will bias the elongated members 630, 632 back to the neutral position.

The angle or curvature of the first elongated member 630 and the second elongated member 632 may be adapted as desired for a given application. For a surgical implant device for use in a spinal motion preservation system, the curvature or angle of the members may be configured to follow the curvature of the spine. In the depicted embodiment, curvature of the first elongated member 630 and the second elongated member 632 is along a constant radius.

FIG. 28 illustrates a fifth embodiment of a dynamic stabilization device 810. The device 810 illustrated in FIG. 28 is similar to the device 410 illustrated in FIG. 20 except that the device includes a pair of flexible joints. Having a device with multiple flexible joints may provide increased range of motion of the device, both pivotally and axially, as compared to a device with a single flexible joint.

The device 810 includes a first elongated member 830a movably attached to a second elongated member 832 and a third elongated member 830b movably attached to the second elongated member. The first, second, and third members 830a, 832, 830b may be configured in a variety of ways. Any members capable of being movably attached to each other while also being attached to other system components to provide controlled movement between the components may be used. In addition, the device 810 may have more than two flexible joints and three members.

In the depicted embodiment, the first elongated member 830a is realized as a first rigid rod, the second elongated member 832 is realized as a second rigid rod attached to the first rod by a first housing portion 834a, and the third elongated member is 830b is realized as third rigid rod attached to the second rod by a second housing portion 834b. The device 810 also includes one or more bump stops 838a and one or more resilient members 840a associated with the first housing portion 834a and one or more bump stops 838b and one or more resilient members 840b associated with the first housing portion 834b. In the depicted embodiment, the one or more bump stops 838a, 838b and the one or more resilient members 840a, 840b may be realized as generally annular or doughnut-shaped components similar to the bump stops 438 and resilient member 440 illustrated in FIG. 15. Other shapes and other configurations, however, are possible.

In the depicted embodiment, the configuration and operation of the connection between the first and second members 830a and 832 is substantially similar to the connection between the third and second members 830b and 832. Furthermore, the configuration and operation of both connections illustrated in FIG. 28 are substantially similar to the connection between the first member 430 and the second member 432 in the embodiment of FIGS. 14-20 (discussed above). Therefore, the disclosure of the configuration and operation of the embodiment of FIGS. 14-20 sufficiently describe the configuration and operation of the embodiment of FIG. 28.

Modification and alterations will occur to others upon a reading and understanding of this specification. It is intended to include all such modifications and alterations insofar as they come within the scope of the appended claims or the equivalents thereof.

The invention claimed is:

1. A surgical implant device for use in a motion preservation system, comprising:
   a first elongated member having a first end and a second end;
   a second elongated member having a first end and a second end, wherein the second end of the first elongated member is adjacent the first end of the second elongated member;
   a housing having a first end and a second end, the first end of the housing being connected to the first end of the second elongated member, the second end of the housing defining an opening, wherein the second end of the first elongated member is disposed within the housing such that the first elongated member is axially movable and pivotally movable relative to the second elongated member;
   a flange disposed around the first elongated member in the housing;
   resilient members disposed concentrically around the first elongated member in respective grooves on each side of the flange in the housing, wherein the resilient members resist relative movement of the first elongated member relative to the second elongated member, and wherein one of the resilient members and respective grooves is an end resilient member and an end groove, the end resilient member being disposed in the end groove, the end resilient member protruding beyond an end face of the first elongated member and contacting an end face of the second elongated member; and
   a stop surface adjacent the opening that limits the relative pivotal movement of the first elongated member relative to the second elongated member.

2. The device of claim 1, wherein the end resilient member is positioned between the flange and the end face, and wherein the flange compresses the end resilient member against the end face when the first elongated member is moved relative to the second elongated member.

3. The device of claim 1 further comprising a second end face and a shoulder, wherein two of the resilient members are positioned between the flange and the second end face, and the two resilient members are positioned between the flange and the shoulder.

4. The device of claim 1 wherein the housing further comprises an inner surface and wherein the end resilient member prevents the first elongated member from directly contacting the inner surface as the first elongated member moves relative to the second elongated member.

5. The device of claim 1 wherein the resilient members are elastomer rings.

6. The device of claim 1 wherein at least one of the elongated members is adapted to attach to an osseous anchoring device.

7. The device of claim 1 wherein the housing is threadably attached to the second elongated member.

8. The device of claim 1 further comprising a retaining portion associated with the second elongated member to retain the first end of the second elongated member within the housing.

9. The device of claim 1 wherein the first elongated member is adapted to connect to a pedicle screw anchored in a first vertebra and the second elongated member is adapted to attach to a pedicle screw anchored in a second vertebra.

10. A surgical implant device for controlling movement between a first bone or tissue portion and a second bone or tissue portion, the device comprising:
    a first elongated member connectable for movement with the first bone or tissue portion;
    a second elongated member connectable for movement with the first bone or tissue portion;
    a housing connected to the second elongated member, the housing having an inner surface, wherein an end of the first elongated member is disposed within the housing and wherein the first elongated member is axially movable and pivotally movable relative to the second elongated member;
    a flange disposed around the first elongated member within the housing; and
    resilient members positioned concentrically around the first elongated member in respective grooves on each side of the flange within the housing between the end of the first elongated member and the inner surface of the housing, the resilient members preventing the first elongated member from contacting the inner surface of the housing when the first elongated member moves relative to the second elongated member, wherein the resilient members resist relative movement of the first elongated member relative to the second elongated member, and wherein one of the resilient members and respective grooves is an end resilient member and an end groove, the end resilient member being disposed in the end groove, the end resilient member protruding beyond an end face of the first elongated member and contacting an end face of the second elongated member.

11. The device of claim 10 further comprising a second end face and a shoulder, wherein two of the resilient members are positioned between the flange and the second end face, and the two resilient members are positioned between the flange and the shoulder.

12. The device of claim 10 wherein the resilient members are elastomer rings.

13. The device of claim 10 wherein the first elongated member is adapted to connect to a pedicle screw anchored in a first vertebra and the second elongated member is adapted to attach to a pedicle screw anchored in a second vertebra.

14. A surgical implant device for use in a motion stabilization system, comprising:
    a first elongated member having a first end and a second end;
    a second elongated member having a first end and a second end;
    a housing attached to the first end of the second elongated member, wherein the second end of the first elongated member is received within the housing;
    a flange disposed around the first elongated member in the housing;
    resilient members disposed concentrically around the first elongated member in respective grooves on each side of the flange in the housing, wherein the resilient members resist relative movement of the first elongated member relative to the second elongated member, and wherein one of the resilient members and respective grooves is an end resilient member and an end groove, the end resilient member being disposed in the end groove, the end resilient member protruding beyond an end face of the first elongated member and contacting an end face of the second elongated member; and
    a means for limiting pivotal movement of the first elongated member relative to the second elongated member.

15. The device of claim 14 wherein the housing defines an opening though which the first elongated member extends and wherein the means for limiting pivotal movement circumscribes the opening.

16. The device of claim 14 wherein the resilient members are elastomer rings.

* * * * *